US00PP35151P2

(12) United States Plant Patent
Keil

(10) Patent No.: US PP35,151 P2
(45) Date of Patent: May 2, 2023

(54) ***SCINDAPSUS* PLANT NAMED 'SILVER BABY'**

(50) Latin Name: *Scindapsus pictus*
Varietal Denomination: Silver Baby

(71) Applicant: Tristan Keil, Mattituck, NY (US)

(72) Inventor: Tristan Keil, Mattituck, NY (US)

(73) Assignee: Emma's Garden Growers, Inc., Huntington, NY (US)

( * ) Notice: Subject to any disclaimer, the term of this patent is extended or adjusted under 35 U.S.C. 154(b) by 13 days.

(21) Appl. No.: 17/803,537

(22) Filed: Aug. 16, 2022

(51) Int. Cl.
*A01H 5/02* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373, 263.1
CPC ..... A01H 5/02; A01H 5/12
See application file for complete search history.

*Primary Examiner* — Kent L Bell
(74) *Attorney, Agent, or Firm* — James R. Holm

(57) ABSTRACT

A new and distinct *Scindapsus* plant named 'Silver Baby' particularly distinguished by unique silverish-blue leaf coloration with some slight greenish colored blotches on the upper surface of mature leaves, silvery and iridescent leaf sheen across the entire leaf surface, and semi-compact and trailing growth habit, is disclosed.

4 Drawing Sheets

Genus and species: *Scindapsus pictus.*
Variety denomination: 'Silver Baby'.

BACKGROUND OF THE NEW PLANT

The present invention comprises a new and distinct variety of *Scindapsus* plant, botanically known as *Scindapsus pictus*, and hereinafter referred to by the variety name 'Silver Baby'.

This new *Scindapsus* plant was discovered by the inventor as a naturally occurring whole plant mutation (sport) of an unnamed and unpatented *Scindapsus pictus* plant derived from a vegetative cutting and grown in a greenhouse in Suffolk County, N.Y. The discovery of the new plant was made by the inventor in February 2021 in a non-publicly accessible area of a commercial greenhouse located in Suffolk County, N.Y.

The new cultivar was selected based on its distinctive shiny and silverish-blue leaf coloration with silvery and iridescent leaf sheen across the entire leaf surface. 'Silver Baby' was first reproduced asexually using meristem tip cuttings in Suffolk County, N.Y. in March 2021. Asexual propagation by meristem tip cuttings of the new variety has shown that the unique features of the new variety are stable and reproduced true-to-type to date through six successive generations.

Plant Breeder's Rights for this variety have not been applied for. 'Silver Baby' has not been made publicly available or sold anywhere in the world more than one-year prior to the effective filing date of this application.

SUMMARY OF THE INVENTION

The new *Scindapsus* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Scindapsus* variety. The combination of these characteristics distinguishes 'Silver Baby' as a new and distinct variety of *Scindapsus:*

1. Unique shiny and silverish-blue leaf coloration with some slight greenish colored blotches on the upper surface of mature leaves;
2. Silvery and iridescent leaf sheen across the entire leaf surface; and
3. Semi-compact and trailing growth habit.

DESCRIPTION OF THE PHOTOGRAPHS

This new *Scindapsus* cultivar is illustrated by the accompanying-colored photographs which show the overall appearance and distinct characteristics of the plant. The colors shown are as true as can be reasonably obtained by conventional photographic procedures. The photographs are of a 2-month-old plant grown in a 4-inch round container under moderate shade in a glass covered greenhouse in Suffolk County, N.Y. Colors in the photographs may differ slightly from the color values cited in the botanical description which accurately describes the colors of the new variety.

Figure 1:
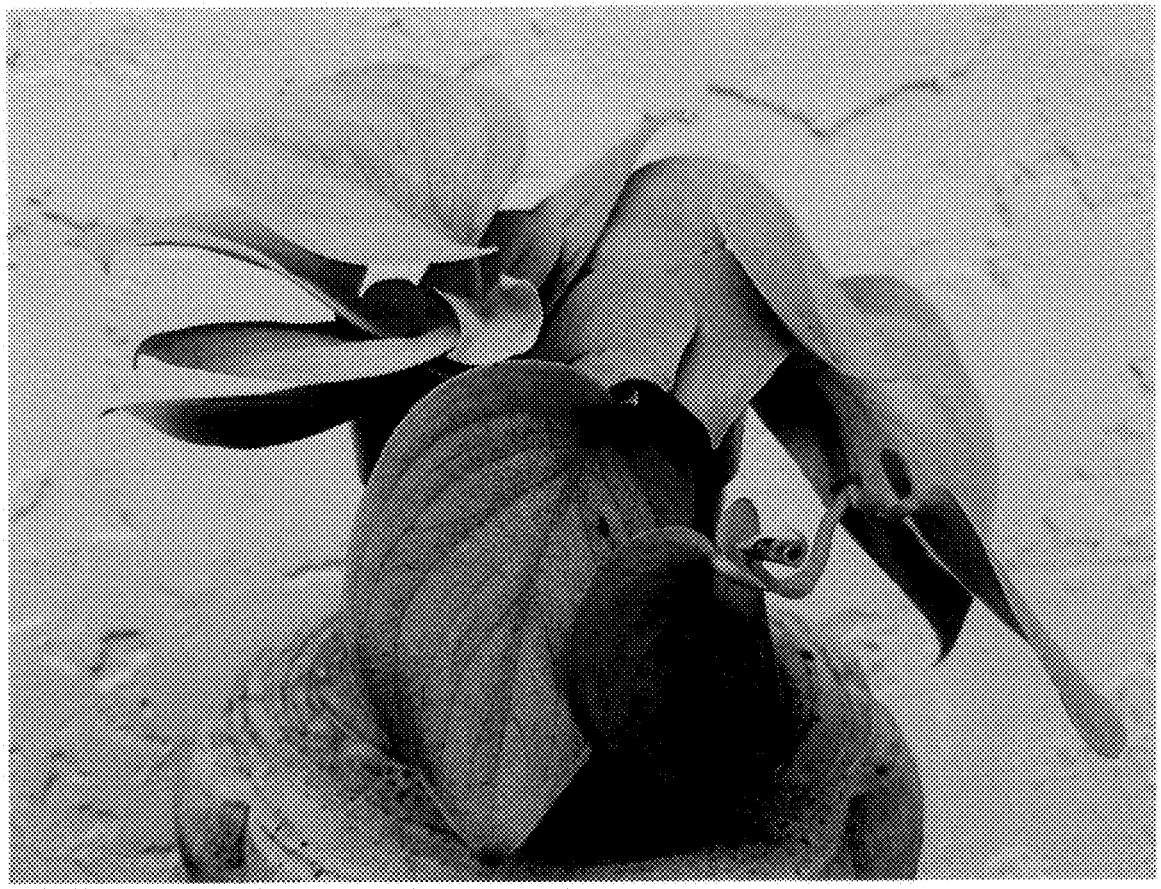

FIG. 1. shows a side view of the overall plant form and foliage of 'Silver Baby'.

Figure 2:
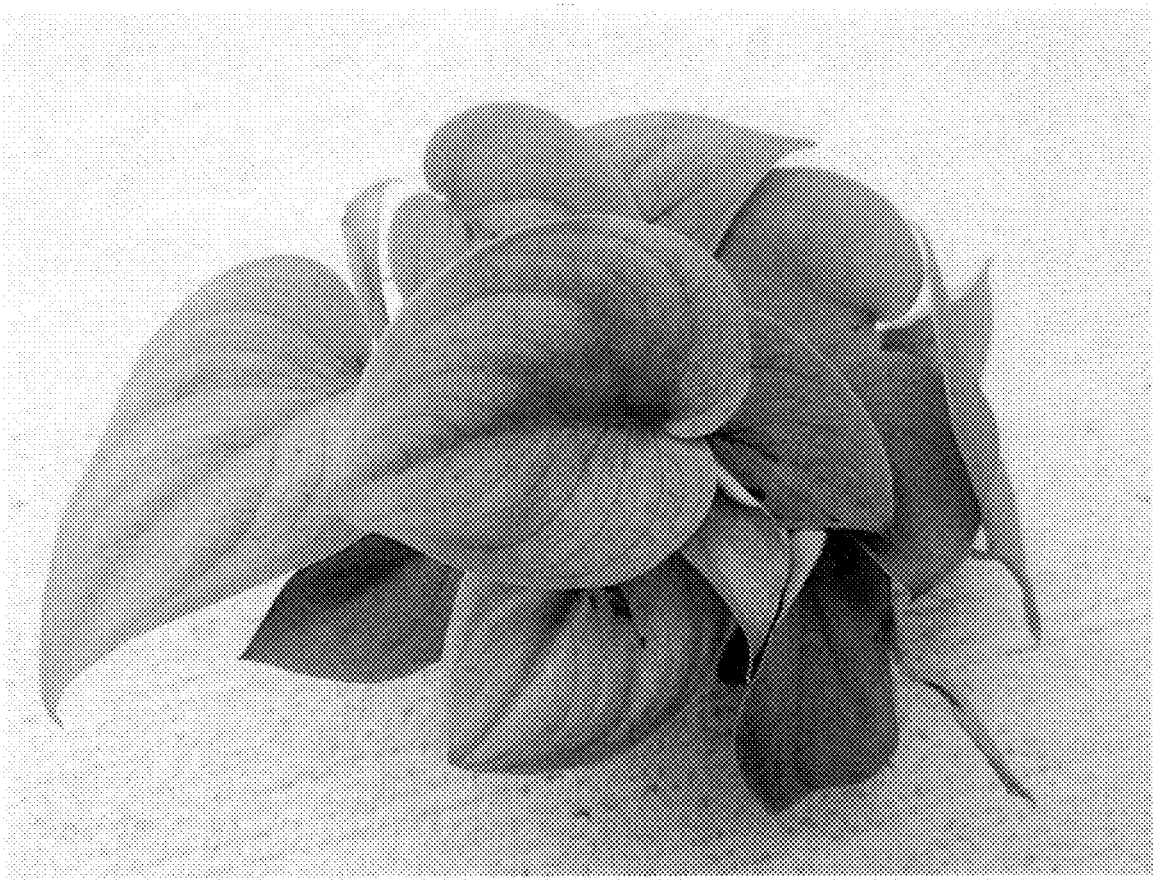

FIG. 2. shows a top view of the overall plant form and foliage of 'Silver Baby'.

Figure 3:
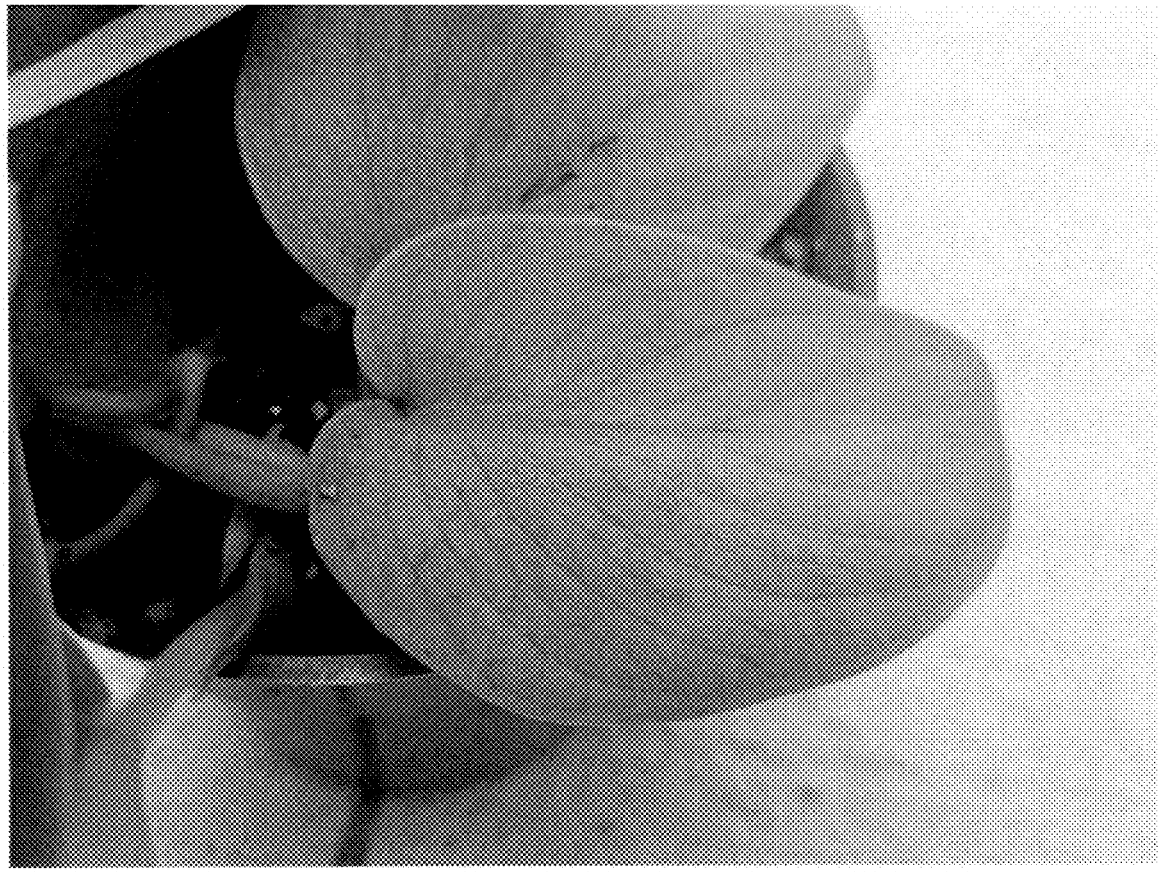

FIG. 3. shows a closeup of a mature leaf of 'Silver Baby'.

Figure 4:
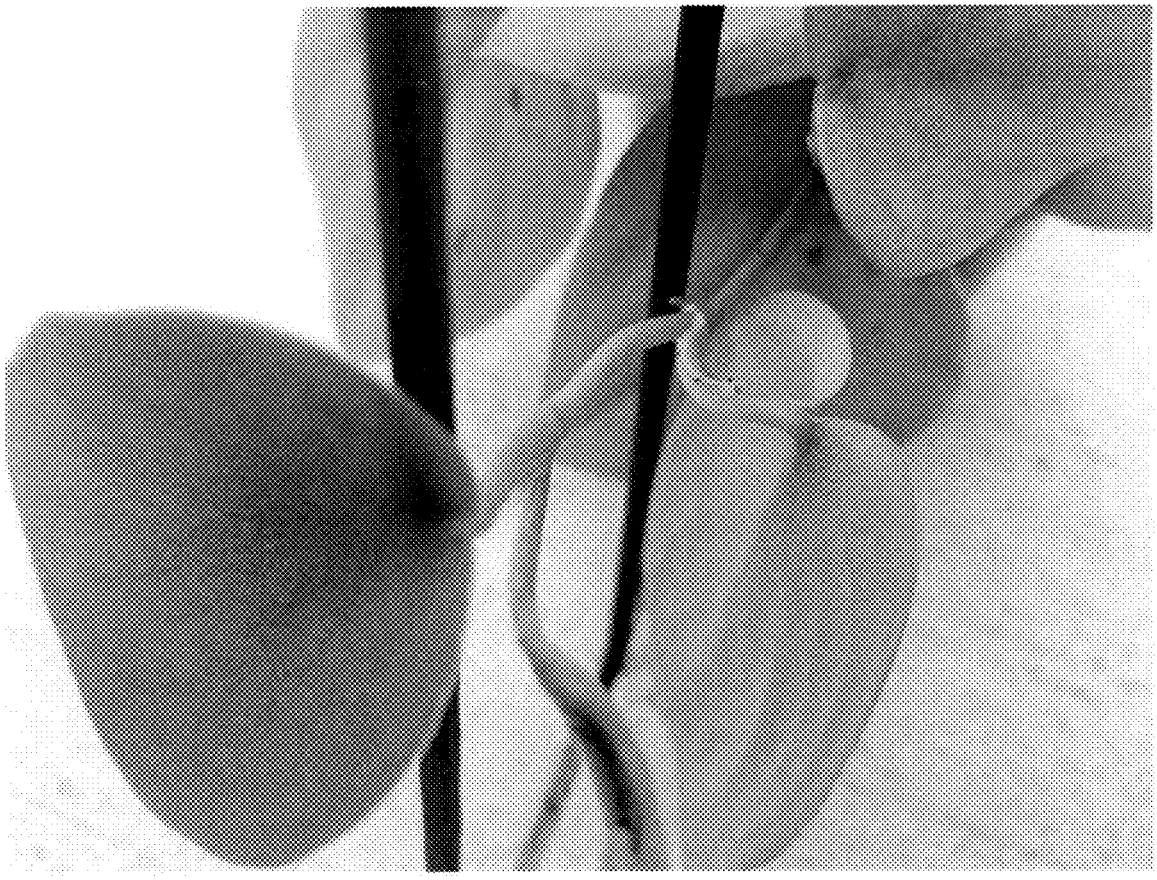

FIG. 4. shows a closeup of a typical vine of 'Silver Baby'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown under moderate shade in a glass covered greenhouse in Suffolk County, N.Y. Detailed descriptions were taken in May 2022 from a 2-month-old plant grown in a 4-inch round container. Measurements and numerical values represent averages of typical plant types.

DETAILED BOTANICAL DESCRIPTION

Classification:

*Family*.—Araceae.

*Botanical.—Scindapsus pictus.*

*Common.—Scindapsus.*

*Denomination*.—'Silver Baby'.

General description:

*Plant type*.—Perennial tropical vine.

*Growth habit*.—Semi-compact and trailing.

*Height from soil level to top of foliar plane*.—Approximately 7.62 cm.

*Plant spread*.—Approximately 12.7 cm.

*Growth rate*.—Moderate, approximately 6.35 cm of stem growth per month.

*Branching characteristics*.—One main stem, weak basal branching.

*Diameter of stems*.—0.32 cm.

*Length of stems*.—About 12.7 cm on a 2-month-old plant.

*Internode length*.—2.54 cm.

*Texture of stems*.—Rounded, smooth, moderately glossy.

*Color of stems*.—Yellow-green, 138A to 138B.

*Number of leaves per stem*.—5 on a vine measuring 12.7 cm.

*Propagation type*.—Meristem tip cuttings.

*Time to produce a rooted cutting*.—2 weeks at an average of 75 degrees Fahrenheit.

Foliage description:

*Arrangement*.—Alternate, simple.

*Attachment*.—Petiolate.

*Lamina*.—Shape: Cordate. Length: Mature leaf: 6.35 cm to 8.89 cm. Immature leaf (newly expanded): 5.0 cm to 6.35 cm. Width: Mature leaf: 6.35 cm to 7.00 cm. Immature leaf (newly expanded): Approximately 4.45 cm. Aspect: Young leaves slightly concave, older leaves mainly flat. Apex shape: Acute. Base shape: Slightly lobate, open area between lobes is shallow, about 0.32 cm to 0.48 cm in depth. Texture (both upper and lower surfaces): Slightly rugose, velvety. Orientation: Held horizontal to slightly downward. Margins: Entire. Color: Juvenile foliage (both upper surface and lower surfaces): Pale green, 189B. Mature foliage (both upper and lower surfaces): Pale green, 189B, with a slight background fading to moderate yellow-green, 143D, as leaves mature. Upper and lower surface leaf sheen: Lustrous with a silvery iridescence. Venation: Pattern: Arcuate. Color, upper surface: Dark yellow-green, 189A. Color, lower surface: Moderate olive green, 137A.

*Petiole*.—Length: 3.18 cm. Width: 0.32 cm. Color: Yellow-green, 143C to 143D. Sheath: Length: Approximately 0.95 cm to 1.27 cm from point of attachment on the stem to the tip of the sheath. Color: Greenish white, close to 155C, and translucent along edges.

*Aerial roots*.—One aerial root nodule present at each node, approximately 0.16 cm in length and colored brown-orange, N167A.

Inflorescence: None observed.

Cold tolerance: None observed.

Disease and pest tolerance: None observed.

Fruit and seed set: None observed.

Drought tolerance: None observed.

COMPARISON WITH PARENTAL VARIETIES

'Silver Baby' differs from the parent *Scindapsus* plant in that 'Silver Baby' has leaves that are nearly all silver, whereas the parent *Scindapsus* plant has leaves that are green with small spots of silver.

COMPARISON WITH COMMERCIAL VARIETIES

When 'Silver Baby' is compared to the commercial *Scindapsus* plant 'Silver Hero' (unpatented), 'Silver Hero' has larger leaves that are more matte and less iridescent than the leaves of 'Silver Baby'.

I claim:

1. A new and distinct variety of *Scindapsus* plant named 'Silver Baby', substantially as illustrated and described herein.

* * * * *